United States Patent [19]

Oita

[11] 4,110,431

[45] Aug. 29, 1978

[54] WET WEATHER RESISTANT BINDER COMPOSITION FOR ADHERING A PLANT TREATMENT ADDITIVE POWDER FORMULATION TO PLANT FOLIAGE

[75] Inventor: Katashi Oita, Seattle, Wash.

[73] Assignee: Weyerhaeuser Company, Tacoma, Wash.

[21] Appl. No.: 741,185

[22] Filed: Nov. 12, 1976

[51] Int. Cl.² .............................................. A01N 9/10
[52] U.S. Cl. ........................................ 424/78; 424/95; 424/131; 424/141; 424/148; 424/264; 424/362; 424/364
[58] Field of Search ................ 424/78, 148, 131, 141, 424/195, 95, 362, 364

[56] References Cited

U.S. PATENT DOCUMENTS

| | | | |
|---|---|---|---|
| 2,098,836 | 11/1937 | Ressler | 424/78 |
| 3,980,773 | 9/1976 | Oh et al. | 424/95 |

OTHER PUBLICATIONS

Dupont Technical Information Bulletin–PV7–369.
Dupont Technical Bulletin "Elvanol–Grades & Specifications".
Stein–Hall "Jaguar Derivatives"–Specification Sheet.
Kirk–Othmer–Encyclopedia of Chem. Tech. 2nd ed., vol. 21, 1970, p. 362.
Chemical Abstracts 74:76953m (1971).
Chemical Abstracts 68:3450m (1968).

*Primary Examiner*—Leonard Schenkman

[57] ABSTRACT

A wet weather resistant binder composition and method, for adhering a plant treatment additive formulation that is substantially water-insoluble such as an insecticide, pesticide or ruminant repellent to plant foliage, is described. The binder composition is a dry powder mixture of a water-soluble polymer having a cis diol structure such as polyvinyl alcohol at about 30–70 weight percent and a water-soluble inorganic metal salt such as borax or chromic nitrate at about 2–10 weight percent, weight percentages based on the combined weight of the binder composition and additive formulation. The binder composition is dry-mixed with a dry powdered plant treatment formulation and broadcast onto plant foliage wherein, upon contact with water either already on the foliage or in subsequent rains, the binder composition dissolves and reacts to form an insoluble didiol complex matrix in which the insoluble additive formulation is bound and adhered onto the foliage to be treated.

1 Claim, No Drawings

WET WEATHER RESISTANT BINDER COMPOSITION FOR ADHERING A PLANT TREATMENT ADDITIVE POWDER FORMULATION TO PLANT FOLIAGE

BACKGROUND OF THE INVENTION

This invention relates to compositions and methods useful for treating plant foliage with an insoluble powdered additive formulation to protect the plant from damage by insects, pests, diseases and browsing animals. More particularly, the invention is useful in binding an insoluble powdered additive formulation to a plant to be protected in such a way that it may be applied during wet or dry weather and is thereafter resistant to washing off in subsequent wet weather.

In the cultivation of plants for food, shelter products, paper or ornamental display it is frequently necessary to protect the plants from disease, insects, and, in some cases, from animal browsing. A common approach is to apply a biologically active formulation to the plant foliage to be protected, which formulation contains a bio-active material that effects a desired result such as, for example, killing an insect infestation. If the purpose of the formulation is long-term effectiveness rather than a quick one-time control, fixing an extended-life active material onto plant foliage becomes a difficult problem with respect to the weather. Rainfall tends to wash the active materials from the foliage and into the soil where it generally has little effect on foliage-attacking pests or disease. Thus, in order to continue protection of valuable plants, subsequent applications of active materials must be made. As the active materials are often poisonous to non-target insects, animals and/or man, repetitive applications usually have undesirable ecological side effects. Excess bio-active material may eventually find its way into drinking water supplies or into food resources, causing cumulative effects on certain birds or animals as overly repetitive applications run off into surrounding soils and into surface or ground water.

To minimize runoff resulting from rainfall it is necessary first of all to use a form of the active material that is substantially water-insoluble. Many protective formulations are applied in a liquid form with the active ingredient emulsified or suspended in an organic solvent-emulsifier with the balance of the formulation made up with water. Where long-term effectiveness is desired and the weather is unfavorable, quick-drying solvents have been used to help ensure the active material is dried onto the foliage before the next rain. If the active ingredient dries to a solid that is substantially insoluble in water, it may form a relatively tenuous mechanical bond to the foliage and exhibit some resistance to mild rainfalls.

Since the active ingredient is usually a very small portion of the applied composition, an insoluble filler with some weather-resistant adhesive characteristics to help bind the active material to the plant foliage is useful. Of course, such a binder material must not be phytotoxic with respect to the plant to be protected. As an example, in Ressler, U.S. Pat. No. 2,098,836, an insecticidal composition is described which includes a polyvinyl alcohol at about 0.2 to 2 percent by weight of an aqueous solution of nicotine. The addition of the polyvinyl alcohol is said to improve the effective life of the insecticide, after it has dried in place, by forming a relatively insoluble film that protects the active-nicotine from loss from the plant foliage through volatilization and the washing action of rain.

SUMMARY OF THE INVENTION

The improved binder composition of this application is useful for adhering an insoluble powdered additive formulation onto plant foliage for long-term protection of the plant from attack by disease, insects, browsing animals or for other purposes. The dry, powdered binder composition is: (1) a cold water-soluble polymer having a cis diol structure, for example polyvinyl alcohol or a guar gum derivative, constituting 30–70 percent by weight of the combination of an additive formulation and the binder composition; and (2) a water-soluble inorganic metal salt such as borax, chromic nitrate or soluble dichromates, constituting 2–10 percent by weight of the combination wherein the salt in the presence of water dissolves and reacts with the polymer in aqueous solution to form an insoluble didiol complex. The improved binder composition is dry-mixed with the additive formulation, which formulation may comprise an active compound or material of a type and of a quantity sufficient to accomplish a desired biological or other result and a filler or bulk material generally added as a diluent to make the active material easier to handle and more likely to be uniformly distributed.

The binder composition may be modified by the addition of an insoluble but water-swellable polymer which improves wet weather resistance by providing water-absorbing capability immediately upon contact with water allowing added time for the binder materials to dissolve and react before losses through the washing action of the water can occur.

The method of using the above binder composition and additive formulation combination requires intimate mixing of the dry powder ingredients, followed by broadcasting the combination onto plant foliage, preferably previously wetted, in an amount sufficient to accomplish the purpose of the active additive ingredient.

The basic objective of the improved combination of the binder composition and active additive formulation is to provide a means for binding the additive formulation to an object to be protected so that it remains in place after a rainfall, thus increasing the effective life of the active additive formulation component.

Further, the improved composition allows application of the active additive formulation relatively independently of wet weather conditions, such as during moderate rainfalls.

The combinations suggested are non-phytotoxic and allow a plant to freely continue growth.

DESCRIPTION OF THE PREFERRED EMBODIMENT

The improvement is a two-component binder composition in the form of a dry powder mixture that is combined with a powdered, insoluble additive formulation selected to accomplish a certain objective with respect to a plant. The combination of binder composition and additive formulation is dusted onto plant foliage to be treated, using a conventional manual or power-operated duster such as those commonly used in farming operations. In operation, the well-mixed dry powder combination is applied to plant foliage most effectively after the foliage has been wetted by rain, fog or dew. It also may be applied during fog or rainfall. Application during extremely heavy rain, at about 1 inch of rain per hour, is not recommended, however. The combination may be applied during dry weather to dry foliage but, if so, some loss due to wind scattering is to be expected, reducing the effectiveness of the application.

The principal requirement of the improved binder composition is the formation of a water-insoluble didiol complex that is the product of a solution of a polymer having a cis diol structure of the type

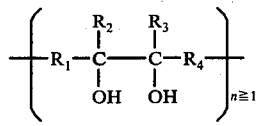

wherein $R_1$, $R_2$, $R_3$, and $R_4$ are any alkyl, aryl, halogen or hydrogen that permits formation of the insoluble didiol and a water-soluble metal salt, such as borax, or other effective complexing salt such as those indicated below.

A preferred embodiment of the improved binder composition comprises a dry mixture of cold water-soluble polyvinyl alcohol and borax. With respect to the total combination weight of binder composition and additive formulation, the polyvinyl alcohol component constitutes about 30–70 percent by weight of the total combination while the borax component constitutes 2–10 percent by weight.

When the borax and the cold water-soluble polyvinyl alcohol contact water, both dissolve and then react to form a water-insoluble didiol complex, as indicated below:

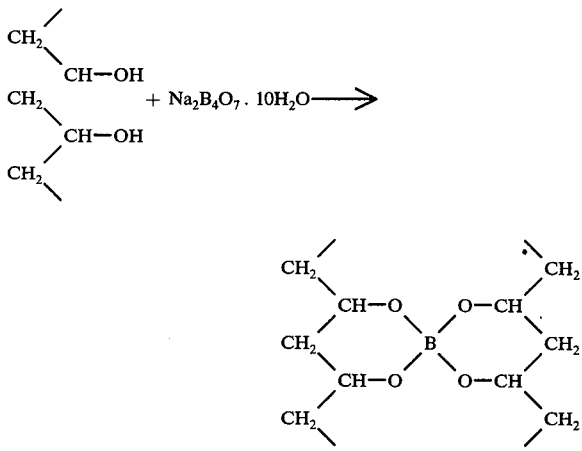

The didiol precipitates out of solution trapping the additive formulation in a matrix which dries to a hard, substantially water-insoluble, film-like material. The matrix material binds itself to the foliage through interfacial molecular attractive forces and, perhaps to some extent, by mechanically gripping the relatively rough foliage surface or encapsulating small conifer foliages.

The above binder composition is improved by the addition to the combination of a water-absorbent but insoluble polymer, in the range of 2–15 percent by weight of the total combination. The incorporation of the water-absorbent or swellable polymer improves the wet weather resistance of the combination by allowing added time for the polyvinyl alcohol-borax system to dissolve, react and form the water-insoluble matrix before washoff during a heavy rain occurs. The typical water-swellable polymer is capable of absorbing many times its own weight of water before becoming saturated. Thus, the swellable polymer, which is selected to have inherent adhesive or "tacky" qualities of its own, immediately binds the combination to the wet foliage, when applied during a rain, or to dry foliage as rain initially begins to strike the powdered surfaces. By the time the polymer absorbency limit is reached, the PVA-borax mixture will have reacted forming the didiol complex which binds the additive formulation into a matrix fixed to the foliage. Upon exposure to dry weather the absorbent polymer will lose water to form a hard film. In a following rain, the polymer will swell as it again absorbs water. The ability of the polymer to reabsorb water, to soften and swell, is an advantage over a binder matrix which is permanently hard and water-insoluble. When a hard, water-insoluble film forms on the growing tips of trees, for example, subsequent growth is hindered. When the film on the growing tip contains the water-swellable polymer, the film will soften in heavy fog or rain and permit the enveloped bud and needles to grow more normally.

The improved binder composition has been found to be most useful in combination with a ruminant repellent formulation to protect growing tree seedlings from being browsed. A preferred repellent formulation for protecting Douglas fir from deer browsing is an insoluble powdered, inedible, dried whole chicken egg. These formulations and their effectiveness as repellents are described in U.S. Pat. No. 3,980,773 by Oh, et al. entitled "Ruminant Repellent From Fresh Lipoidal Material," incorporated herein by reference for the purpose of establishing the effectiveness of the inedible dried egg as a repellent and describing the testing procedures used to establish efficacy with respect to animal browsing.

The following examples describe the improved composition in combination with the inedible egg deer repellent and its effective use in protecting Douglas fir foliage from being eaten by deer. The first three examples employ a deer browse test technique called a Pen Tree Test Bioassay which comprises exposing a plant foliage test arrangement to wild deer held captive in a pen under near natural conditions. A 10-acre tract, containing 15–20 head of wild black-tailed deer, is subdivided into a 4-acre section and 2 3-acre bioassay sections. Native trees and shrubs such as Douglas fir, vine maple and salal partially cover the pen area, while water and supplemental food for the deer are also provided. The level of stocking with deer is 20–50 times that observed in the wild to ensure a high feeding pressure. The foliage test arrangement comprises branches as repellent substrates fastened to stakes which are spaced 2 feet apart and arranged in rows. Three rows, spaced 4 feet apart, form a block with each 3-acre section containing two blocks at right angles to one another. Each repellent trial involves sufficient replications and controls to ensure statistically reliable results.

Examples 1 and 2 indicate the effectiveness of the various binder compositions in combination with the bio-active egg formulation in protecting Douglas fir over an extended period of time, in comparison with untreated controls. Examples 3 and 4 indicate the effectiveness of the improved binder compositions after exposure to artificial rainfall (Example 3) and long-term weathering (Example 4). The Example 4 tests utilized a field bioassay technique in which the four listed test locations each comprise a 5-acre open site divided into 10 half-acre plots each planted with about 500 Douglas fir seedlings ranging from 1-3 years of age. The plots are randomly selected for treatment or controls. Browsing pressure is provided by the native local deer populations which are free to move through the unfenced plots. The test period spanned late May through mid-July at scattered growing plantations throughout western Washington, insuring exposure of the test plots to repeated rainfall.

The basis of the instant improvement is a composition of a mixture of two water-soluble powdered components that, upon dissolution together in water, react to form a water-insoluble matrix that adheres itself and any included insoluble active additive formulation to plant foliage, despite the presence of excess water or continuing impingement of rainfall. The reacting composition components and resulting matrix must be nontoxic to plants to be protected. Also, they must be compatible with the active formulation, both chemically and physically. Of course, the binder composition components must be capable of quickly going into solution and reacting to form the insoluble binder matrix before the entire combination washes from the plant foliage. Thus, materials must be selected for rapid dissolving characteristics under conditions of minimum or no agitation.

The preferred polyvinyl alcohol component of the binder composition may be any cold water-soluble material that is finely ground such as Gelvatol 20-30 BP and 20-90 BP produced by Monsanto Corporation or Elvanol 50-42 produced by DuPont of Wilmington, Del.

Polymers, other than polyvinyl alcohol, that are water-soluble, have the cis diol structure and are capable of complexing to form an insoluble didiol matrix may be used in the improved combination so long as the polymers are not phytotoxic to the plants to be protected. For example, derivatives of natural guar gums complexed well in experimental trials. A quaternary ammonium guar derivative (Jaguar C-13, Mfg. by Stein-Hall Co. of New York, N.Y.) and a carboxymethylhydroxypropyl guar (Jaguar CMHP) showed indications of results comparable with the polyvinyl alcohol polymers.

The precipitating component is preferably borax and any commercial grade is satisfactory that is ground to a particle size of less than 1mm in diameter. Other inorganic metal salts may be used to cause the gellation of a cis diol polymer or the polyvinyl alcohol to an insoluble film. Chromic nitrate, ammonium, potassium or cupric dichromate and cuprammonium hydroxide are effective.

Effective combinations of the improved binder composition and active deer repellent formulation contained a polyvinyl alcohol concentration of about 55 percent by weight of the combination. Adequate binders were made with polyvinyl alcohol concentrations in the range of 30-70 weight percent. The preferred concentration of the borax precipitating agent was 5 percent by weight of the combination, with a range of 2-11 percent providing effective precipitation. The ratio of polyvinyl alcohol to borax preferred was 11:1 with a usable ratio range of 15:1 to 7:1.

The water-swellable polymer is an important improvement to the basic binder composition when application during rainfall is contemplated. The preferred water-swellable material is an anionic starch derivative such as SGP 502S made by General Mills Chemicals, Inc. of Minneapolis, Minn. with a particle size of about 74 microns capable of holding 500 times its own weight of pure water, or up to 50 times of a 0.9 percent saline solution. Upon exposure to dry weather, the SGP 502S material loses water to form a hard matrix component which in subsequent rains swells as water is reabsorbed. Many materials may be used that have these desired characteristics such as a cross-linked acrylamideacrylic copolymer, wood flour, paper pulp, clay, charcoal, zeolite, talic and silica. The preferred concentration was discovered to be at about 9 percent by weight of the applied combination binder and active formulation. A range of 2-15 percent by weight of the combination has been found to be effective.

Minor quantities of nonessential components may be included in the combination such as, for example, a water-insoluble, fine particle sized, highly visible pigment dye. Its purpose in the deer repellent formulation is to make the treatment visible so that the degree of coverage can be determined.

Since the basic improvement described herein is the binder composition and its use in conjunction with any insoluble additive formulation that accomplishes a desired result with respect to treatment of plants, the examples are not intended as limiting the scope of this improvement as only effective with the deer repellent. Any pesticide, insecticide or other type protectants or repellents or marking dyes, etc. may be bound to plant foliage utilizing the binder of this application, where long-term effectiveness would otherwise be diminished by rain removal of the active ingredient.

Example 1: Pen Tree Test Bioassay

Application Method: Powder combination dusted onto moistened Douglas Fir branches; 16 branches per treatment block. See Pen Tree Test Bioassay design described above.

| | Combination Components, Weight Percent | | | | | | Percent Foliage Browsed, Indicated Hours Exposure | | | | | | |
|---|---|---|---|---|---|---|---|---|---|---|---|---|---|
| No. | Egg | PVA[1] | Borax | Swellable Polymer | Other[4] | | 20 | 24 | 44 | 68 | 92 | 116 | 140 |
| 1 | 33.0 | 55.0 | 11.0 | 0 | 1.0 | Treated | 0 | 0 | 0 | 6 | 31 | 44 | 44 |
| | | | | | | Control[5] | 0 | 50 | 81 | 87 | 100 | | |
| 2 | 33.0 | 49.4 | 10.0 | 6.6[2] | 1.0 | Treated | 0 | 0 | 0 | 19 | 50 | 56 | " |
| | | | | | | Control | 0 | 50 | 62 | 87 | 100 | | |
| 3 | 33.0 | 49.4 | 10.0 | 6.6[3] | 1.0 | Treated | 0 | 0 | 0 | 13 | 25 | 31 | 38 |
| | | | | | | Control | 0 | 50 | 87 | 100 | | | |
| No. | Egg | PVA[1] | Borax | Swellable Polymer | Other[4] | | 160 | 164 | 172 | 188 | 212 | 236 | 284 |
| 1 | 33.0 | 55.0 | 11.0 | 0 | 1.0 | Treated | 44 | 44 | 44 | 50 | 56 | 63 | 75 |
| | | | | | | Control[5] | | | | | | | |
| 2 | 33.0 | 49.4 | 10.0 | 6.6[2] | 1.0 | Treated | 56 | 56 | 56 | 56 | 56 | 75 | 81 |
| | | | | | | Control | | | | | | | |
| 3 | 33.0 | 49.4 | 10.0 | 6.6[3] | 1.0 | Treated | 38 | 44 | 44 | 50 | 56 | 75 | 81 |

-continued

Example 1: Pen Tree Test Bioassay

Application Method: Powder combination dusted onto moistened Douglas Fir branches; 16 branches per treatment block. See Pen Tree Test Bioassay design described above.

| Combination Components, Weight Percent | Percent Foliage Browsed, Indicated Hours Exposure |
|---|---|
| Control | |

Notes:
[1]Poly Vinyl Alcohol - Elvanol 50-42 manufactured by DuPont de Nemours of Wilmington, Delaware.
[2]Water-Swellable Polymer - Carboxylated Butadene - Styrene Copolymer - Carbopol 934 manufacture by B. F. Goodrich Chemical Company.
[3]Water-Swellable Polymer - Anionic Starch Derivative, SGP 502S manufactured by General Mills.
[4]All formulations contain fluorescent dye.
[5]Controls are untreated Douglas fir branches.

Example 2: Pen Tree Test Bioassay

Application Method: Powder combination dusted onto moistened Douglas Fir branches; 16 branches per treatment block. See Pen Tree Test Bioassay design described above.

Combination Components, Weight Percent — Percent Foliage Browsed, Indicated Hours Exposure

| No. | Egg | PVA[1] | Borax | Swellable Polymer | Other[4] | | 4 | 20 | 28 | 44 | 52 | 68 | 76 | 92 | 100 |
|---|---|---|---|---|---|---|---|---|---|---|---|---|---|---|---|
| 1 | 33 | 55 | 11 | 0 | 1 | Treated | 0 | 0 | 0 | 0 | 0 | 0 | 0 | 0 | 0 |
| | | | | | | Control[5] | 0 | 12 | 25 | 25 | 25 | 100 | | | |
| 2 | 33 | 50 | 16 | 0 | 1 | Treated | 0 | 0 | 0 | 0 | 0 | 0 | 0 | 0 | 0 |
| | | | | | | Control | 0 | 37 | 37 | 37 | 37 | 75 | 75 | 75 | 75 |
| 3 | 20 | 66 | 13 | 0 | 1 | Treated | 0 | 0 | 0 | 0 | 0 | 0 | 0 | 0 | 0 |
| | | | | | | Control | 0 | 12 | 12 | 25 | 25 | 75 | 75 | 88 | 88 |
| 4 | 33 | 49.4 | 10 | 6.6[2] | 1 | Treated | 0 | 0 | 0 | 0 | 0 | 0 | 0 | 0 | 0 |
| | | | | | | Control | 25 | 50 | 50 | 50 | 50 | 75 | 75 | 75 | 75 |
| 5 | 20 | 60 | 12 | 7[3] | 1 | Treated | 0 | 0 | 0 | 0 | 0 | 0 | 0 | 0 | 0 |
| | | | | | | Control | 0 | 25 | 25 | 37 | 37 | 50 | 50 | 50 | 50 |
| 6 | 33 | 49.4 | 10 | 6.6 | 1 | Treated | 0 | 0 | 0 | 0 | 0 | 0 | 0 | 0 | 0 |
| | | | | | | Control | 12 | 37 | 37 | 62 | 62 | 100 | | | |

| No. | Egg | PVA[1] | Borax | Swellable Polymer | Other[4] | | 116 | 124 | 140 | 148 | 172 | 216 | 240 | 360 |
|---|---|---|---|---|---|---|---|---|---|---|---|---|---|---|
| 1 | 33 | 55 | 11 | 0 | 1 | Treated | 0 | 0 | 0 | 0 | 0 | 13 | 25 | 88 |
| | | | | | | Control[5] | | | | | | | | |
| 2 | 33 | 50 | 16 | 0 | 1 | Treated | 0 | 0 | 0 | 0 | 0 | 0 | 38 | 88 |
| | | | | | | Control | 75 | 75 | 75 | 75 | 100 | | | |
| 3 | 20 | 66 | 13 | 0 | 1 | Treated | 0 | 0 | 0 | 0 | 0 | 0 | 25 | 88 |
| | | | | | | Control | 100 | | | | | | | |
| 4 | 33 | 49.4 | 10 | 6.6[2] | 1 | Treated | 0 | 0 | 0 | 0 | 0 | 0 | 12 | 75 |
| | | | | | | Control | 88 | 100 | | | | | | |
| 5 | 20 | 60 | 12 | 7[3] | 1 | Treated | 0 | 0 | 13 | 13 | 13 | 13 | 13 | 75 |
| | | | | | | Control | 88 | 88 | 100 | | | | | |
| 6 | 33 | 49.4 | 10 | 6.6 | 1 | Treated | 13 | 13 | 13 | 13 | 13 | 13 | 13 | 88 |
| | | | | | | Control | | | | | | | | |

Notes:
[1]Poly Vinyl Alcohol - Gelvatol 20-30 BP manufactured by Monsanto.
[2]Water-Swellable Polymer - Anionic Starch Derivative - SGP 502S, manufactured by General Mills Chemicals, Inc.
[3]Water-Swellable Polymer - Crosslinked Starch - 35A-100, manufactured by Grain Processing Corp.
[4]All combinations included a fluorescent dye.
[5]Controls are untreated Douglas fir branches.

Example 3: Pen Tree Test Bioassay

Application Method: Douglas Fir seedlings, potted bare root nursery stock with an average of 7 new growth shoots 1" in length. Treated seedlings were wetted, powdered heavily, then dried.
Seedlings were then selectively exposed to artificial rainfalls of indicated duration.
After rainfall treatment all treated seedlings and untreated controls were subjected to Pen Tree Test Bioassay design described above.
Combination Components: 33% Powdered Egg; 49.4% Poly Vinyl Alcohol; 10% Borax; 6.6% Water-Swellable Polymer; and 1% Flourescent Dye.

| No. | Repellent Powder Applied | Sprinkler Soaking, Minutes | 39 | 63 | 72 | 96 | 144 | 168 | 192 | 216 | 255 | 304 | 336 | 360 | 384 |
|---|---|---|---|---|---|---|---|---|---|---|---|---|---|---|---|
| 1-2 | No | None | 20 | 20 | 20 | 60 | 60 | " | " | " | " | " | " | " | " |
| 2-3 | No | None | 80 | 80 | 80 | 80 | 80 | " | " | " | " | " | " | " | " |
| 3-7 | Yes | None | | | | | | | | | | | 20 | 35 | 50 |
| 4-8 | Yes | 10 Min. | | | | | | | | | | 6 | 12 | 50 | |
| 5-9 | Yes | 20 Min. | | | | | | | | 6 | 6 | 6 | 13 | 38 | 56 |
| 6-10 | Yes | 30 Min. | | | | | | | | 5 | 11 | 21 | 37 | 42 | 47 |

Example 4: Field Bioassay

Douglas fir seedlings were treated just prior to spring growth, and browsing results observed after six weeks' exposure.

Combination Components: 33% Powdered Inedible Egg; 55% Quaternary Ammonium Guar Derivative (Jaguar C-13, Mfg. Stein-Hall Co. New York, N.Y.); 5% Borax; 9% Anionic Starch Derivative (SGP 502-S mfg. General Mills Co. Minneapolis, Minn.); and 1% Dye.

| Test Location | | % of Trees Browsed Since Treatment Applied | Days of Exposure | % Damage[3] Reduction |
|---|---|---|---|---|
| Pioneer Creek | Control[1] | 31 | 54 | 80.6 |
| | Treated[2] | 6 | | |
| Wilson Creek C400 | Control | 11 | 62 | 81.8 |
| | Treated | 2 | | |
| Wilson Creek C1700 | Control | 11 | 62 | 90.9 |
| | Treated | 1 | | |
| Wilson Creek A800 | Control | 1 | 65 | o[4] |
| | Treated | 1 | | |

Notes:
[1]Controls were untreated Douglas fir seedlings.
[2]Treated with combination commpositions of this invention, as indicated above.
[3]$\% \text{ Damage Reduction} = \frac{100 \times (\% \text{ of controls browsed}) - (\% \text{ of treated seedlings browsed})}{(\% \text{ of controls browsed})}$
[4]Indicates essentially no browsing pressure during period.

What is claimed is:

1. A method for adhering an insoluble active formulation to plant surfaces comprising:

applying to said surfaces, being wetted by rainfall of less than one inch per hour, a uniformly mixed dry powder combination of an effective amount of the water-insoluble formulation and a binder composition, said binder comprising, an inorganic metal salt that is water-soluble, selected from the group consisting of borax, chromic nitrate, cupric dichromate and cuprammonium hydroxide, and a polymer that is cold water-soluble having a cis diol structure selected from the group consisting of polyvinyl alcohol, quaternary ammonium derivative of guar gum and carboxymethylhydroxypropyl guar gum, whereupon the cis diol polymer and metal salt components of the binder dissolve in water on said plant surfaces and then react to form an insoluble matrix of the binder composition and insoluble formulation, which matrix adheres to said plant surfaces resistant to subsequent rainfall, said polymer and said metal salt being present in an amount to form said insoluble matrix upon contact with water.

* * * * *